US008381319B2

(12) United States Patent
Stein

(10) Patent No.: US 8,381,319 B2
(45) Date of Patent: Feb. 26, 2013

(54) COOLING SYSTEM WITH A COVER WHICH CONTAINS SUPER ABSORBER AND CAN BE ACTIVATED

(75) Inventor: Gabriele J. Stein, Elchingen (DE)

(73) Assignee: Pervormance International GmbH, Ulm (DE)

( * ) Notice: Subject to any disclaimer, the term of this patent is extended or adjusted under 35 U.S.C. 154(b) by 1325 days.

(21) Appl. No.: 11/920,251

(22) PCT Filed: May 12, 2006

(86) PCT No.: PCT/EP2006/004510

§ 371 (c)(1), (2), (4) Date: Nov. 13, 2007

(87) PCT Pub. No.: WO2006/120020

PCT Pub. Date: Nov. 16, 2006

(65) Prior Publication Data

US 2009/0090018 A1 Apr. 9, 2009

(30) Foreign Application Priority Data

May 13, 2005 (DE) ......................... 10 2005 023 025

(51) Int. Cl.

| | |
|---|---|
| ***A62B 17/00*** | (2006.01) |
| ***F26B 19/00*** | (2006.01) |
| ***F26B 21/08*** | (2006.01) |
| ***A61L 9/04*** | (2006.01) |
| ***A47B 81/00*** | (2006.01) |
| ***D06B 23/00*** | (2006.01) |

(52) U.S. Cl. ................. 2/458; 62/316; 62/259.3; 34/60; 34/557; 428/34.7; 428/35.7; 239/55; 312/115; 312/31.1; 312/237; 134/95.2; 68/6; 68/5 D; 68/5 C

(58) Field of Classification Search .................... 62/316, 62/259.3; 34/60, 557; 428/34.7, 35.7; 239/55; 312/115, 31.1, 237; 134/95.2; 68/6, 5 D, 68/5 C; 2/458

See application file for complete search history.

(56) References Cited

U.S. PATENT DOCUMENTS

| | | | | |
|---|---|---|---|---|
| 3,103,450 | A * | 9/1963 | Janson | 68/5 C |
| 3,632,041 | A * | 1/1972 | Radford et al. | 239/128 |
| 3,660,013 | A * | 5/1972 | Payet et al. | 8/116.4 |
| 3,868,835 | A * | 3/1975 | Todd-Reeve | 68/20 |
| 3,884,632 | A * | 5/1975 | Payet et al. | 8/116.4 |
| 4,523,441 | A * | 6/1985 | Braybrook et al. | 68/5 C |
| 5,345,995 | A * | 9/1994 | Yano et al. | 165/46 |
| 5,606,746 | A | 3/1997 | Shelton et al. | 2/102 |
| 5,669,894 | A * | 9/1997 | Goldman et al. | 604/368 |
| 5,704,230 | A * | 1/1998 | McClain et al. | 68/5 C |
| 5,755,110 | A * | 5/1998 | Silvas | 62/259.3 |
| 5,832,552 | A * | 11/1998 | Haselwander | 8/149.3 |

(Continued)

FOREIGN PATENT DOCUMENTS

| | | |
|---|---|---|
| DE | 36 27 940 | 3/1988 |
| DE | 691 04 851 | 4/1995 |

(Continued)

*Primary Examiner* — Marc Norman
*Assistant Examiner* — Filip Zec
(74) *Attorney, Agent, or Firm* — Jacobson Holman PLLC

(57) ABSTRACT

The invention refers to a cover, comprising a fleece arranged between a top and a bottom layer which holds a super absorber. At least in one layer a permeability area which is permeable to moisture is provided through which the cover can be moistened in a controlled way.

6 Claims, 4 Drawing Sheets

U.S. PATENT DOCUMENTS

Figure 8:
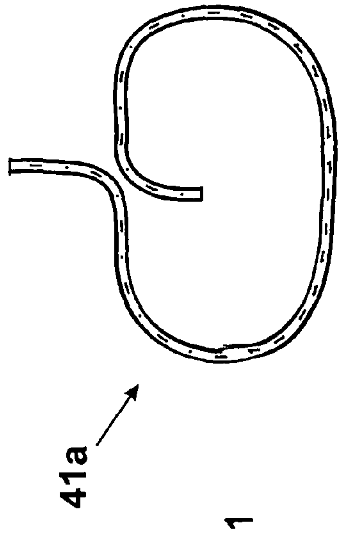

| | | | | |
|---|---|---|---|---|
| 6,109,338 | A * | 8/2000 | Butzer | 165/46 |
| 6,241,554 | B1 * | 6/2001 | Murakami et al. | 439/587 |
| 6,329,565 | B1 * | 12/2001 | Dutkiewicz et al. | 604/378 |
| 6,473,910 | B2 * | 11/2002 | Creagan et al. | 2/458 |
| 6,955,067 | B2 * | 10/2005 | Davenet et al. | 68/17 R |
| 2002/0076533 | A1 | 6/2002 | Caceres et al. | 428/195 |
| 2002/0112499 | A1 * | 8/2002 | Goldfine | 62/316 |
| 2004/0000175 | A1 * | 1/2004 | Bolduan et al. | 68/5 D |

FOREIGN PATENT DOCUMENTS

| | | |
|---|---|---|
| DE | 200 22 620 | 4/2002 |

* cited by examiner

COOLING SYSTEM WITH A COVER WHICH CONTAINS SUPER ABSORBER AND CAN BE ACTIVATED

This is a national stage of PCT/EP06/004510 filed May 12, 2006 and published in German.

The invention refers to a cover comprising a fleece which is arranged between a top and a bottom layer, equipped with a super absorber and absorbs moisture or liquid.

Covers as clothing for cooling man or animal is already state of the art.

I. STATE OF THE ART

This clothing or generally cover consists as a rule of an interior lining filled with super absorber crystals or gel, or is made from a specific material containing super absorber and an exterior shell which may consist of very different materials such as cotton, micro fiber, incombustible fabric or other materials.

Here the particular property of the super absorber for binding water and to release it again only by evaporation is used. By the evaporation of the water at high temperatures latent heat occurs which causes, when such a material is worn, for example, at the body in the form of a garment, a cooling effect on the skin.

All these garments have in common that the material, before it can be used, has to be activated by water. This is done, as a rule, by soaking the garment for some time in water. Often the soaking time must not be exceeded much as then the super absorbers may drain off. The thus prepared cover, it may be, for example, a garment or even a piece in the size of a towel or a handkerchief, often cannot be worn comfortably on the skin. The surface is wet and exudes on its surface also moisture and/or super absorber to the skin leading to an uncomfortable feeling of wearing.

In particular if pressure is exerted, for example, on the garment, for example, by carrying luggage or heavy outer garment the result is a feeling of wetness.

Basically the known garments would be interesting, for example as a protective clothing in a fire brigade operation. Because of the problems described in the beginning, however, these products do not have the suitable success on the market.

II. OBJECT OF THE INVENTION

It is an object of the invention to increase the applicability of the covers mentioned before.

III. SOLUTION ACCORDING TO THE INVENTION

In order to solve this problem the invention suggests several different individual ways of solution.

First of all it is suggested that the cover which is equipped as described has at least at one side a permeability area which is permeable to moisture so that the cover can be moistened in a controlled way.

It has been found that the poor acceptance of the known covers leads to the fact that these products feel "wet" when used. By means of the suggestion according to the invention it is achieved that the moisture is introduced in one or more preferred point(s) in the cover, and not necessarily the entire surface of the cover has to be moistened. By means of the suggestion of the invention to introduce the moisture actually at a particular side in the cover the permeability area provided for that purpose is arranged exactly at a point which does not interfere in an uncomfortable way, for example during use of the cover.

The result is, however, a cover the surface of which is not wet from the beginning and does not lead to an uncomfortable feeling when worn.

Furthermore the invention comprises also an activation chamber which consists of a lock-up interior space, and serves for holding one or more covers. This activation chamber, which can be designed, for example, like a cabinet, suitcase, chest or box, serves for activating the fleece of the cover accordingly. The aim is to prepare the cover in such away, that means to activate, that a cooling potential as large as possible is available without causing uncomfortable feelings during the operation. In order to achieve this the activation chamber is equipped with a moistening device for moistening the cover, and/or a drying device, in particular for a superficial drying of the cover. Each of the two modifications suggested solve the problem presented in the beginning on their own, and are, of course, also in combination very advantageous.

It is an aim of the procedure to automatically activate the super absorber in the cover, for example, by water, and to dry the exterior shell of the cover only superficially. Thus the result is a cover dry on the outside, which, however, contains internally sufficiently liquid to achieve the desired cooling effect by latent heat without producing wetness or water drops during use.

The problem presented in the beginning, however, is also solved by a method for activating a cover. According to the invention it is suggested here that the activation, first of all, contains a moistening or watering of the cover comprising a fleece with a super absorber absorbing moisture or liquid, and, after that, drying of the surface of the cover is carried out. Of course, it is important here that, if possible, only one surface is dried, and from the deeper area of the cover no water or other liquid is removed as, by means of that, the cooling capacity or the cooling potential is reduced accordingly. It is an advantage here that the used super absorbers hold back the water even under pressure that means they cannot be wrung out.

The problem according to the invention presented in the beginning is also solved by an activation system or cooling system comprising a cover as described, and an activation chamber also as described. The cover here is loaded with moisture or a liquid (e.g. water) in the activation chamber in a controlled and adjusted way so that, after removing the cover from the activation chamber, because of the necessary evaporation heat for evaporating the loaded liquid, a cooling potential exists. This cooling potential is then made available for, e.g., the person wearing this jacket, for example a fire fighter, so that the performance of this person increases considerably which results in a corresponding increasing of the work protection for the person in such hazardous operations.

It is an essential element of the invention that the cover is suitable for being loaded in an activation chamber with liquid in order to provide the user of the cover in an operation by the evaporation of the liquid out of the cover with a cooling potential. The evaporation heat is absorbed, for example, from the body of the wearing person and leads there to a suitable cooling.

The purpose according to the invention is already reached with a very simply designed cover which can be loaded in a very simply designed activation chamber with liquid, for example, by a very simple time control, and be prepared accordingly on the surface. However, the invention also comprises very intelligently designed solutions where the activation process is triggered by an RFID chip arranged in the cover, if necessary, in co-operation with an information circuit, if namely this cover is hung in an adequately equipped activation chamber communicating with the RFID chip.

In the following these embodiments will be described in detail.

IV. ADVANTAGEOUS EMBODIMENTS OF THE INVENTION

In a modification of the cover according to the invention it is provided that especially in the permeability area means for passing liquid or moisture, for example with an accordingly high hygroscopicity, are provided in order to distribute the liquid as continuously as possible and also rapidly in the fleece. If namely the liquid or moisture is distributed comparatively fast in the fleece, there will be no or only a small risk of wetting the layer forming the top or bottom side. Here in particular the hygroscopic properties of the super absorber can be used, or even materials with a higher hygroscopic behaviour can be used. It is, for example, possible to provide material with a smaller density of super absorber in the fleece in the permeability area where the liquid, that means the water, enters the cover, and thus to obstruct not too much the water passing capacity because of the bulking super absorber. The result is here possibly a cover with inhomogeneous distribution of super absorber.

An essential advantage of the invention is in particular the fact that the fleece can be loaded or moistened with liquid in a controlled way, that means monitored and intended. The use in the hygienic field cannot be seen as controlled according to the present case. The cover furthermore effects that the absorbed liquid is yielded again through evaporation, and the environment is cooled by withdrawing the evaporation heat.

In a preferred modification of the invention it is provided that the permeability area consists of fabric absorbing liquid. To put it exactly the fabric has to guide the liquid to the fleece so that then it can be stored in the super absorbers. Thus it is actually provided to realize either partly or on the whole surface a heterogeneous top and bottom layer, that means that the permeability area consists of another material than the remaining layer.

The invention here comprises solutions which use the same material on the top and bottom layer, that means have a suitable permeability area all over. Also such covers with a completely homogeneous surface which have accordingly good water absorbing but also water steam yielding properties are comprised by the invention.

As an alternative to the supply of moisture or liquid by a suitable fabric it is provided in another modification according to the invention that the permeability area is designed as connection member, in particular for a hose coupling. Such a connecting zone is, for example, also secured by a suitable self-closing valve, and arranged at the cover at a point where it does not interfere (with regard to comfort of wearing, but also visibility from outside). Of course such connection members can also be arranged "hidden" in a pocket.

The connection member is, for example, designed comparatively simply, and simply realized by a snap connection, similar to the one for example used in gardening. The cover moulded for example as jacket or vest is here suspended, for example, on a hanger in the activation chamber, and the liquid is passed through the connection member in the jacket. An effective distribution of the water occurs here as the liquid already gets in the interior of the cover. Possibly here it can be done without an additional drying of the exterior layer surfaces.

Furthermore it is, in particular, provided according to another modification according to the invention that in the fleece and/or between fleece and bottom or top layer, and/or in the bottom and/or in the top layer, in particular channel-like free spaces or perforated hoses leading away from the permeability area are provided. By means of a channel system in the cover designed like this distributing the liquid in the cover is accelerated accordingly, and the time required for re-loading of a suitable cover is reduced clearly. Conveniently this channel system is connected with the permeability area, that means with the area where the liquid is passed in the cover, and more closely to the permeability area the required cross sections are larger and then are reduced further accordingly. Such a design can be realized with a permeability area designed as connection member as well as with a permeability area formed by a fabric accordingly permeable to liquid. Cleverly, in the modification where the area of permeability is designed as hose connection or connection member in the cover also a channel system formed accordingly by hoses and so on is provided. Here the channel-like free spaces or the perforated hoses can be included either in the fleece or between the fleece and the respective layer, or even in the respective layers themselves. In this respect the invention can be designed very variably.

The invention is not restricted in the connection with the design of the permeability area. The permeability area is designed, for example, two-dimensional, or top or bottom layer are equipped on a large surface with at least one permeability area. Such a design is in particular convenient when the respective layer is sprayed or rained on for re-loading the liquid in the cover as the liquid then can enter the cover on a large surface. The necessary way for storing the liquid then in the fleece containing the super absorber is very small. It is, for example, provided there that more than 30% of the layer are equipped with one or more permeability areas. Conveniently, however, also more than 50% of at least one layer can be designed as permeability area. The efficiency for storing the liquid is increased accordingly. Also a cover which has a complete permeability area is part of the invention.

As far as in the following water is discussed the invention is restricted in no way by this. Water has to be understood in this respect as a synonym for each kind of liquids. Also the terms "to moisten" or "to water" are identical, the purpose is here to express that the liquid is passed into the cover.

As far as in the frame of this application moistening or moisture or liquid are discussed these terms are always to be understood synonymously and extensively. As a rule, water is used as liquid, however, also other liquids may be used, in this respect the invention is not restricted, either. A large amount of water or moisture or liquid stored in the fleece, of course, increases the cooling potential.

First of all, by means of a moistening device provided according to the invention in the activation chamber it is achieved that the cover is moistened in a controlled, purposeful way, and the contained super absorbers are loaded heavily with liquid in order to generate a long lasting cooling effect. It is an aim of the arrangement to introduce liquid in the cover in such a way that an enduring cover, dry on the outside (only the surface) results. If the moistening device is designed in interaction with the cover in such a way that the moisture or wetness enters the fleece as directly as possible the result will be a non-wet surface in the first place. It is, in particular, an advantage if liquid has to be passed in a comparatively large, two-dimensional cover, think, for example, large tarpaulins or the like, to build in the cover a suitable hose or tube system so that the superficies surfaces of these lines are perforated in such a way that the water or the liquid can leave at any point, and thus even a comparatively large cover can be activated much faster, that means can be loaded with liquid and activated.

In a very simple design of the invention it is provided that a cover is purposefully moistened and superficial dried in the described activation chamber. Such a combination according to the invention does not require other elements at the cover, loading the cover with liquid is reached by a suitable time interval control.

The activation chamber, however, can also "only" have the function of drying. That means the activation chamber serves for drying the surfaces of covers, which are drenched in order to store water in their interior to such a degree that the result is a comfortable feeling when wearing them without losing the liquid in the interior.

By combining these two suggested steps in such a way that, first of all, the moistening device loads the cover with moisture or liquid, and, after that, only a superficial drying is carried out, these two steps are optimized and coordinated. The result is a cover dry on the exterior which has stored in the interior one, two or more liters of water which can be used for physical cooling through the evaporation heat.

A big advantage of the use of the activation chamber is in particular the fact that moistening is done in a controlled way, and thus, for example, over night or also in a very short time (for example 2-10 minutes for one jacket) a cover can be prepared, loaded, that means activated, in advance. This presents a considerably larger field of use for the covers according to the invention. So far, the known covers have only been used, for example, in the leisure time for reducing large personal heat and so on. However, if now it is provided that the cover is supplied readily prepared, that means stored with corresponding liquid provided for evaporation other fields of use are possible, for example, in the protection of labour, in the fire brigade and so on. In the case of operation, the fire fighter can remove the already readily prepared, loaded and activated cover from the activation chamber, so that, of course, the performance of the person protected in this way is improved or the protection of labour is increased accordingly. As the exact time of the operation of the fire brigade cannot be predicted and through the pressing time manual activation is not possible the activation chamber is an essential advantage for the heat protection of the fire brigade.

Furthermore, the activation chamber according to the invention provides that the cover is dried by the drying device in such a way that the interior of the cover further contains liquid, in particular water, when used actively, and the drying does not drain the fleece material of the water necessary for cooling. In contrast to cabinets known from the state of the art which achieve a preparation of outer garments, in the activation chamber according to the invention a complete drying of the cover is actually avoided. By such a complete drying process namely the cover would be drained off the liquid providing the cooling potential. An essential aspect of the invention is namely the fact that the cover removed from the activation chamber is wet inside.

Ideally the activation chamber reaches such a preparation of the cover automatically, the cover being then stored a suitable time in the activation chamber. By means of a control the complete process is always repeated when the vest does not fulfill its cooling function anymore, that means that it has lost too much water in the interior of the cover. At the same time the cover is stored reliably with access at any time. However, it is also possible to dry again the cover completely in the activation chamber, if it is, for example, designed as garment, that means to remove also the liquid from the super absorber, and to air the cover accordingly in order to avoid a possible infection with germs or mould, if this is necessary, and this effect cannot be reached by other measurements. In order to avoid this, advantageously a climatic control is provided in the activation chamber in a modification according to the invention.

Besides a sequential order of the moistening and drying step in an alternative according to the invention it is provided that moistening and drying are carried out simultaneously. Thus, for example, it is provided that the moisture or the liquid is passed in the permeability area in the cover, and at the same time, parallel to it the surface of the cover is dried, so that the activation process is accelerated accordingly.

In the process according to the invention it is possible here that the moistening or watering of the fleece or the cover is carried out in a zone which is separated and before drying. The two steps, however, can also be carried out one after the other in the described activation chamber. The method according to the invention here also intends that the cover be formed here already only of the accordingly designed fleece, the surface of the fleece (in this case the surface of the cover) is dried in order to generate a comfortable feeling. In the same way it is, of course, possible to bed the fleece, as described, in a top and a bottom layer of other material. In this case then, of course, this layer material has to be dried as described.

The invention consists, for example, first of all, of a special super absorber material which is light and flexible so that it can be used for garments and blankets, medical products, tarpaulins or envelopes for articles. The material used in this invention consists of a synthetic fleece from polyester (carrier fleece) coated with so-called super absorber (super absorbing polymers=SAP). These are networks of flexible, hydrophilic polymerides which may be ionic as well as non-ionic. These are able to absorb watery liquids and to bind them, and are used for absorbing body liquids in hygienic articles, for example in diapers or the like.

The super absorbing polymer comprises polymerized, α-, β-unsaturated carbon acids or their salt or anhydride.

The super absorbing polymer is selected, for example, from a group comprising polyacrylic acid, a hydrolyzed starch acrylonitrile graft polymer, a starch acrylic acid graft polymer, a saponified vinyl acetate acrylic ester copolymer, a hydrolyzed acrylonitrile copolymer, a hydrolysed acryloamide copolymer, an ethylene maleic anhydride copolymer, an isobutylene maleic anhydride copolymer, a poly (vinyl sulfonic acid), a poly (vinyl phosphonic acid), a poly (vinyl phosphoric acid), a poly (vinyl sulfuric acid), and a sulfonated poly styrene, and their salts and/or mixtures.

Furthermore it is provided that the super absorbing polymer is chosen from the group comprising a poly (vinyl amine), a poly (dialkyle aminoalkyle (meth) acryloamide), a poly (ethylene imin), a poly (allyl amine), a poly (allyl guanidine), a poly (di-methyl di-allyl ammonium hydroxide), a quaternary poly styrene derivate, a guanidine modified poly styrene, a quaternary poly methacrylic amide or an analogous ester, a poly (vinyl guanidine), their salts and/or their mixtures.

It is also provided that the super absorbing polymer comprises a poly acrylic acid, neutralized at 50% to 100%.

The super absorber synthetic fleece used in this invention is designed in such a way that the super absorber is bound fixedly in the polyester material. By means of that also the water is bound fixedly without the risk of draining off. It is here a stable, but light and flexible material which can be processed simply, which can be cut and sewed, and thus is perfectly suited for the use in clothing, equipment like in helmets or tarpaulins, blankets or coverings. The outer shell made from one or two materials, serves as a wrapping for the super absorber synthetic fleece.

The basic material forming the fleece as well as the top and/or bottom layer may be all kinds of synthetic fibers, for example polyester, micro fibers, or even another material. It is also possible that fibers of organic origin, for example cotton, wool or the like, are used.

The fibers used for the fleece or top or bottom layer are, for example, of vegetable or animal origin. For example, seeds, bast or hard-fibers, but also suitable wool, hair, or silks can be used. In the field of vegetable fibers it is possible to use cotton, kapok, coconut fibers, but also flax, hemp, ramie fiber or jute. Also the use of cellulose fibers is basically possible. Besides the natural fibers of biologic origin, of course, also mineralic fibers, for example based on glass, asbestos or mineral wool can be used. Such materials are actually in use for fire protection clothing, for example for fire brigades, but also as professional wear in metallurgical plants and so on. Of course, it is also possible to use natural fibers, for example wool or silk, for the cover according to the invention.

Besides the before mentioned fibers of natural origin, of course, also chemically produced fibers can be used. Part of these are, for example, fibers from synthetic polymers like poly amides (trademarks Nylon or Perlon), polyester (PE), poly vinyl chloride (PVC), polypropylene (PP), and/or polyethylene (PE). The fleece material as well as the material of the bottom or top layer of the cover according to the invention are each made from one material or from a mixture of just a few or several of the fibers mentioned before. Because of the large selection of different fiber materials, for the fleece material as well as for the material of the bottom or top layer, there is a large range of possible uses and applications of the cover according to the invention. In particular the material of the top and/or bottom layer consists preferably of a textile material which has a good permeability to water steam, and allows a fast superficial drying.

As super absorber, in particular cross-linked sodium poly acrylates, have proved to be advantageous. They are characterized in particular by a high compatibility when used with persons. However, also other accordingly safe super absorbers can be used. Also poly acrylonitriles can be used as super absorbers.

The cover according to the invention has here a fleece which is equipped with the super absorber. The super absorber is here worked in in very different ways in the fleece. First of all, there is the possibility that the super absorber is processed bound, for example, as gel or crystals in the fleece, or, in another modification according to the invention, the fiber of the fleece is coated with the super absorber. Here all kinds of bonds of super absorber with any fleece at all are discussed.

Furthermore also a wrapping is pulled over the super absorber synthetic fleece, and is produced in the suitable size as wrapping, and thus provides the cover according to the invention. These may be here natural or synthetic fibers like cotton or synthetics, but also, for example CS material, Goretex, aluminum or also fireproof or hardly inflammable materials, as well as other possible outer shells which can also be, for example, impermeable to water and/or air on one of both sides. The selection of the outer shell is done with reference of the use in the cooling situation and may vary. Additionally, the material is when it is readily wrapped, stitched closely or, depending on the material of the wrapping, attached in another way so that the synthetic fleece is held fixedly in the cover.

Besides clothing and equipment, as for example, an interior part of helmets, special wrappings can also be produced as described, for articles as for example cars, EDP installations and so on, which then can be pulled quickly over the objects, and offer instant protection against heat, for example in fires. In order to protect the object in this case absolutely against any water for fire fighting, the bottom side of the wrapping, (for example outer shell 1), that means the side facing the object to be protected is, if necessary, impermeable to water. The top side of the wrapping (for example outer shell 2), opposite the object, will be permeable to air and water in order to guarantee absorbing and evaporation of the bound water, and thus to produce the cooling effect.

Also heat protections as cut goods or in the shape of blankets and tarpaulins can be produced in a similar way leading to a use as heat and/or fire protection covering.

The fleece in this modification of the invention is hardly inflammable, and has, in dry condition, properties similar to polyester with a flaming point of 500° C. as well as a melting temperature of 250° C. The outer shell is, in this case, hardly inflammable or fire proof. By means of that the material can be called already in dry condition as largely fireproof which is important for the field of use.

By the use of the material in the condition activated with water (moist) the flaming point and the melting temperature cannot be determined anymore. Thus the invention has to be called fireproof.

Thus the fire can hit the surface of the fire protection covering directly without damage for the material. The object to be protected is optimally cooled by the high temperature from the outside and the evaporation thus generated by the bounded water, and is not damaged. A further addition of water during fire fighting keeps the effect intact even through the individual evaporation time defined by the first loading.

As the super absorber synthetic fleece can keep the water at normal temperatures up to 24° C. until 60 hours, or at 30° C. almost 40 hours, and thus the cooling effect lasts long this material can be re-used in permanent operation and almost unlimited.

Furthermore the invention provides that the layer consists of textile material, in particular of natural and/or synthetic fibers. The invention is here in no way limited to a special composition. Synthetic as well as natural materials can be used. It is also possible that suitably coated material is used in the top or bottom layer.

It is convenient here that it is provided that good heat-conducting properties are provided at least in the layer facing the article to be cooled. A suitable heat conducting property of just this layer results in a high efficiency, and just the article to be cooled is drained off heat effectively which is needed for the evaporation process of the liquid.

In a preferred modification of the invention it is provided that the cover has a pocket-like recess and the permeability area is arranged in this recess. Cleverly this recess acts as interface or access zone in order to pass the liquid or moisture in the cover. If now, for example, this is arranged in a pocket-like recess, the arrangement can be chosen in such a way that it does not interfere when the cover is used, for example, as protective clothing or the like. The recess is, for example, buttoned up during operation so that the recess, if it is still wet, is not uncomfortably interfering. It is, for example, possible, that a cover designed as jacket is hung inside out or upside down, and the water does not enter the jacket through the interior lining but through the outer shell.

The recess, however, can also be used for hanging the cover. If, for example, the cover is designed as garment, like a vest, jacket or trousers, a hanger-like holder may be put in the recess and thus carry the cover formed as garment. The result is a corresponding advantage when the cover is activated as the cover, when hung, can at the same time be hung out.

The invention is in no way limited to the way the super absorber is embedded in the fleece. The super absorber is characterized, in particular, by the fact that it can absorb many times, for example five to thirty time or considerably more depending on the degree of coating, its volume as water. By a high degree of moistening or liquid input in the fleece or in the cover thus also other mechanical properties, for example the stability, can be changed, and thus also the property of the cover altogether can be adapted. For example, the stability of the cover, when it is used for example as fire protection tarpaulin, is successfully increased by such a high degree of loading of super absorber that it can co-act as shock absorber, and thus provides an additional advantage by protection against damage.

According to that the invention provides that in the fleece gel or crystals containing super absorber are arranged, or the fleece consists at least partly of fibers coated with super absorber. This fiber material again may be produced synthetically or be of natural origin. For example, sodium polyacrylates with advantageous properties have been used as super absorber material. However, the invention is in no way restricted to this.

It is also an advantage that the invention provides that the cover has ventilation channels. Thus there is the possibility that at least one layer consists, for example, of material impermeable to water or even air. For removing the water steam generated by evaporation then an arrangement of suitable ventilation channels in the cover is provided. These ventilation channels are arranged here in the fleece as well as, if necessary, in the layer.

It is actually convenient here that the ventilation channels serve also for distributing liquid in the cover, as well as, for example, serve as channel-like recesses as described. Thus the ventilation channel is used double.

In another modification according to the invention it is suggested that the cover carries a moisture activating element. This moisture activating element is, for example, a contactless acting means, similar for example to a transponder or the like which interacts, for example, with a control element of the activation chamber. This moisture activating element activates the control element, for example, when the cover is suspended in the activation chamber. Thus it is possible, simply by suspending the cover in the activation chamber, to trigger an automatic activation, that means loading with water, or if necessary drying the surface of the cover.

The invention in particular suggests that the moisture activating element is designed as part of an information circuit, the moisture activating element interacting in particular with a moistening device (for example of an activation chamber). The information circuit suggested according to the invention can take over here additional tasks. A radio connection, for example, makes a wireless data transmission between the moisture activating element or the information circuit and the moistening device possible. In this case the information circuit has the suitable elements necessary for radio transmission like an antenna, data memory, a control unit for sending the respective information.

The invention is here in no way restricted to such an electronically designed moisture activating element. Basically it is also possible that a mechanical, electric, electro-magnetic or electronic moisture activating element is provided according to the invention. It is, for example, by simple mechanic means possible to activate the moistening of the cover. For example, the activating element has an element which is inserted in a corresponding part controlling the valve for passing in the liquid. This modification, designed, for example, according to the lock-and-key principle does without any electronics, and fulfils in the same way the purpose according to the invention. It is also possible here that the moisture activating element is coupled, for example with the permeability area designed as connecting member.

Furthermore it is also provided according to the invention that there is either a wire or a wireless connection between the moisture activating element and the moistening device. It is, for example, possible that the moisture activating element is the combination of a mechanical and an electric part. By means of the mechanical part the valve is opened, by means of the electric part corresponding information is transmitted to the moistening device, and this is done automatically. The corresponding information is then read out by the moisture activating element when it is inserted in the corresponding receiving device in order to control the valve. Contacts which are closed then are the wire connection to the moistening device or (as it can also be seen generally) to its control.

It is convenient here that the information circuit or the moisture activating element is attached in or to the cover waterproof and/or mechanically rigid against bending. Such a design serves for protection and thus also for the reliability of the invention.

In another preferred modification of the invention it is provided that the information circuit has a transmitting and/or reception antenna as well as an energy supply. The energy supply can be designed here either actively or passively, and an active energy supply would be, for example, a suitable energy store like a battery or an accumulator. However, also other arrangements are known which actually are passive and get a suitable energy supply from electro-magnetic radiation. These modifications are also part of the invention. Of course, also suitable combinations are possible, so that, for example, by radiating with electro-magnetic energy an accumulator is charged.

Such concepts mentioned before are known, for example, in the connection with the RFID technology. In a further application of the invention namely here not only an identification of the cover, for example as protection against misuse or as information for authorization, can be realized but by means of a suitable, more intelligent information circuit also other data of the cover, for example during an operation, can be collected and evaluated after that. Depending on the case of application, for example, the maintenance of the cover can be accordingly adapted and optimized. Eventually this will lead to a higher efficiency of the used material and to an accordingly higher work protection of the user using this cover. This is in particular interesting when the covers are used, for example, for protective jackets in fire fighting and so on.

The arrangement of the information circuit is here not one-directional, but bi-directional. Thus actually corresponding information can be read in from the outside via the reception antenna in the information circuit, as well as also corresponding information can be sent out of it via the transmitting antenna.

Furthermore the invention makes it possible not only to identify the jacket by means of the information circuit, but also that the status and functionality in connection with the purpose of the operation and the operation is monitored. At the same time, also the user or applicant is monitored. This is achieved by the fact that during use of the cover continuously via the transmitting or reception antenna of the information circuit data are given to a corresponding control center. Of course, this signal can also be used for position fixing purposes as described.

Thus it is, for example, in another modification of the invention provided that the information circuit comprises sensors, for example for the degree of activation or degree of moisture of the cover, for the temperature of the environment and/or physiologic information of the user like body temperature, pulse rate and so on. The range of application of the information circuit almost has no bounds. By the arrangement of different sensors at the cover, for example for monitoring the degree of activation (the degree of moisture of the cover or the fleece) it is possible to inform the user when there is almost no more liquid left for cooling, and wearing the cover designed as jacket does not give actually the desired effect. By means of the status indicating device, for example, the user is informed accordingly. In this case the status indicating device is cleverly also a part of the information circuit or connected with it. The status indicating device may be also a passive element, for example an element changing colours because of the degree of moisture.

It is furthermore also possible to measure the temperature of the environment by a suitable temperature sensor, and to record it and also to determine in that way which heat zones the user with the jacket has entered.

Also physiologic information of the user, like body temperature, pulse rate and so on can be monitored without any problems by means of the modification according to the invention, and thus, for example, a vital signal can be transmitted which can be homed so that the operation of the user can be monitored better and thus is safer. It is convenient in this respect that signals emitted by the transmitting antenna are also used for position fixing purposes. In the case of operation, for example, several reception antennas are arranged around the seat of fire which make homing of this signal possible. This signal is for example used when the physiologic information changes in such a drastic way that it has to be assumed that there are risks or problems. By permanent transmitting a corresponding signal the user can also be found in different situations, and then, if necessary, also be saved. It has to be taken into consideration here that this field of application is added advantageously to the other field of application of the information circuit where it is namely only desired that the identification information and, if necessary, corresponding sensor information gets from the cover in the control device of the activating chamber in order to carry out there suitable activation steps. That means that these two applications do in no way interfere with each other or overlap, ideally they rather supplement each other.

The invention furthermore provides that the information circuit has a data memory for unchangeable identification features, and/or a data memory for collecting of measure values of the sensors. The embodiment mentioned first is, for example, already provided with transponders. The transponders are equipped with a very long number code which characterizes the transponders definitely. Such a transponder would be here then accordingly part of the information circuit suggested according to the invention. Furthermore it is, however, also possible that the information circuit collects data in a cycle (that means controlled by timing or monitoring) which are measured by the sensors and then filed in a data memory. Of course, there is also the possibility that such measured data are transferred immediately to a corresponding operation control center, or, for example, warning signals are coupled with the location. The advantages arising from that are obvious.

Of course, all other information or signals emitted by the transmitting antenna of the information circuit may be used for position fixing purposes.

Conveniently a frequency range for operating the transmitting or reception antenna from 120 to 135 kHz, 13.56 MHz, 868/915 MHz or 2.45 GHz is used.

The frequency ranges mentioned before are used typically for data or energy transmitting ways with inductive coupled transponders. These are not extremely narrow bands but the transmitting range has a suitable waveband in order to make amplitudes as well as frequency modulation or also digital data transfer possible as free from interference as possible. Typically the waveband can transmit 10 to 20% of the basic frequency.

By the use of a transponder, in particular with a clear identification number or code, there is the possibility of separating authorized covers from unauthorized covers in an activation chamber interacting with it. Thus suitable safety aspects can be realized, and, for example, a corresponding mistreatment of the covers often used as protective jackets or in the work protection can be excluded safely.

The use of a transponder or an information circuit does not only have the advantage that the loading condition of the cover is monitored accordingly, it also allows establishing a suitable monitoring of wear of the cover, and thus to indicate corresponding covers right in time for exchange.

The moisture activating element can be here designed in very different ways. Besides the use of small transmitters, that means active components, it is possible to design the activation element passively, for example like a transponder. In this modification, for example, at a suitable transmitter an antenna is provided from which the activation element gets the energy because of reception of electro-magnetic radiation in order to transmit then itself corresponding information, like an activation information, for the control element.

The essential advantage of such a design is the fact that the arrangement of such an activation element is extremely economical, however, the process in the activation chamber can be controlled in any way by accordingly evaluating the activation element. It is possible, besides the inquiry whether there is a cover in the activation cabinet, also to build a suitable data processing for that. It is, for example, also possible to differentiate definitely a first cover with a first activation element which has been hung at a first time in the activation chamber from a second cover with a second activation element hung at a second time. Thus, for example, the user can see that, for example, the first cover can already be used again as it is loaded and activated, however, the second not yet. The activation element thus not only has the task of triggering corresponding working or activation steps, according, for example, to the process of the invention, but it also serves for individualizing the single covers, and thus for an even more perfect use of the covers according to the invention.

In a preferred modification of the invention it is provided that at the cover a status indicating device is provided. By means of the status indicating device it is possible that the user can see the activation condition. So the user can get the information about how long the cooling effect will last.

Conveniently it is provided here that this status indicating device also interacts with the information circuit, also provided according to the invention, or is provided by this with data or also energy. Thus, for example, an LED lightened by different colours can give information about the loading condition in a simple way.

In another alternative according to the invention for the status indicating device an energy store is provided. It is, for example, possible to combine the activation element designed as transponder with the status indicating device. This is designed, for example, as moisture sensor. By means of the transponder technology it is possible to store electric energy in the capacity elements. By means of that it is possible that the moisture sensor is also charged with energy when the cover is prepared in the activating chamber. By means of this energy it is then possible to determine and also display the loading condition.

Furthermore the problem of the invention is also solved by an activation chamber as described. The activation chamber consists of a lock-up interior space for holding one or more cover(s). The activation chamber can be designed like a cabinet, however, the invention is not limited to that. As far as in the following, for example, a climatic drying cabinet, drying cabinet and so on is discussed this term is to be understood as synonymous with the activation chamber according to the invention.

This climatic drying cabinet serves, on the one hand, for watering and thus activating the materials. On the other hand it serves exclusively for the drying of the outer shell, which is done very fast, without losing water in the interior of the cover, that means interfering with the cooling effect of the synthetic fleece of the super absorber. Drying can be carried out by hot air, immersion heaters or other heat sources suitable for drying, which are controlled accordingly.

All these processes are carried out automatically so that the user does not have to make any effort for activating, drying or storing. Additionally, there is accessibility for 24 hours by the control.

In a preferred modification of the invention it is provided that the moistening device is arranged in or at the holding device holding the cover. This holding device is formed, for example, as hanger, however, it may have also other designs, according to the design of the cover. Cleverly, the holding device is designed, for example, hollow with drillings in the walls through which the liquid can enter the cover. It is, however, also possible to provide, for example, a valve-like arrangement, the valve being opened when the cover is put on the holding device. For example, a moisture activation element designed mechanically and arranged at the cover is inserted in the control element designed as valve and thus opened. In this way also it is possible to activate the loading.

Besides a hanger-like holding device the invention also suggests frame-like or fan-like designed holding devices by means of which a distribution of the moisture as effective as possible is achieved.

It is provided here that the moistening device has a valve which can be controlled, in particular controlled by the weight of the cover. Because of the filling of the cover with moisture the weight of the cover increases. The arrangement is chosen here in such a way that the controlled valve closes when a certain weight is exceeded. Thus it is provided that not unintended too much moisture or liquid gets in the cover, or the activation chamber itself is damaged. Besides a very simple modification, equipped with suitable springs and so on, it is, of course also possible to provide an electronically active weight sensor which then acts in a suitable way on an electrically or electro-magnetically controlled valve.

Besides an arrangement of the moistening device in or at the holding device carrying the cover it is, of course, also possible to provide an effective, hose-like connecting element (as part of the moistening device) interacting with the connection member of the cover (as area of permeability). By connecting then at the same time also a suitable valve is opened, and the cover is loaded with moisture. By means of corresponding weight sensors also here the degree of filling can be monitored, and the valve then again be re-adapted.

The modifications mentioned before are in particularly based on the assumption that the cover is hung, for example, at a holding device orientated vertically. The holding devices, aligned as a rule to the cover, interact then, for example, with an area of permeability provided on the interior side of the cover, and moisten or water thus the cover.

Alternatively to that it is provided in another modification according to the invention that the moistening device carries at least one spray head. The spray head makes a two-dimensional spraying of the cover possible, and allows, for example, a very large area of permeability to be drenched or wetted accordingly with liquid.

The arrangement of a spray head is possible with the suspended, vertically orientated cover. However, it is also possible, when the cover is sprayed on when it is spread, for example, horizontally on a floor provided in the activation chamber for supporting the cover. Thus, for example, a number of floors, one above the other, arranged like shelves can be provided in the activation chamber, for example, the bottom side of the floor carrying the spray heads in order to moisture or water accordingly the cover supported on the floor below.

In another modification it is provided that the floor is part of the moistening device, and has outlets for the liquid. Thus, for example, the floor is shaped like a box, that means it has a hollow body which the liquid can enter, for that purpose the floor is connected with suitable connection means to the pipe system and lines of liquid. Of course, a suitable valve control is provided which effects that the liquid supply can be controlled accordingly.

The moisture activating element according to the invention is here not restricted to only an electronic or electric design, but it can also have a mechanical design, for example may have a valve control activated by a tappet.

The invention comprises here activation chambers designed relatively simply whose activation of the covers is achieved either only by a suitable time or time interval control, or by relatively complex designs. This is achieved in particular by the fact that the climatic control is realized as store programming control (SPS) by means of which, for example, an individual adaptation for the moistening process (for example allowed time interval, degree of loading, in particular for the weight of the cover and so on) is possible.

It is here, of course, provided that the climatic control controls the time interval for the moistening as well as for the drying processes. By a clever interaction of moistening and drying processes the loading process for the cover is accordingly optimized, and the user is provided with a cover at its best.

Furthermore it is provided that the activation chamber has a climatic control. The climatic control can be equipped here with a number of sensors determining the corresponding physical values of the climate prevailing in the interior. These may be, for example, the air moisture, the temperature or also the gas composition. However, it can be also a simple time interval control which sets an individual moistening and/or drying time. Because of this information the climatic control acts on suitable control systems, for example the heating or the moisture or liquid supply for the covers.

Furthermore it is provided that the activation chamber has a climatic control. The climatic control is here equipped with a number of sensors determining suitable physical values of the climate in the interior. This may be, for example, the air moisture, the temperature or even the gas composition.

Because of this information the climatic control acts on suitable control systems, for example heating or the moisture or liquid supply for the covers.

Furthermore, for example, moisture sensors for the cover or weight or mass sensors for the covers are provided in order to measure by means of these sensors the loading condition of the covers. Also the measure values of these sensors are provided to the climatic control as central control of the activation chamber which then, because of this information, for example stops the liquid supply or starts drying. This can be done cleverly in a preferred modification of the invention by a store programming control (SPS).

In another modification of the invention it is provided in particular that the climatic control monitors also the gas composition or air composition in the interior space. For example, in order to prevent the forming of damaging populations of bacteria or mould, it is provided in a modification according to the invention to design the interior space gasproof, and, when the interior space is closed, to generate a suitable protective gas atmosphere which, for example, interferes with or disturbs the development of such germs. By means of that it is possible to fight actively mould, for example on covers which have been suspended in the activation chamber a long time. In such a design the activation chamber then has a connection with a suitable gas supply, or it produces this gas itself by means of suitable devices and compresses, and selects suitable valves.

A modification a bit simpler for avoiding mould on the stored covers is in particular the one that by means of the activation element equipped with a transponder it is actually known when a corresponding cover has been hung in the activation chamber, and the control then has a special drying programme running in order to drain the water stored in the super absorber. When the super absorber, however, is drained from water also the nutrient medium for the reproduction of mould or germs is removed as far as possible.

Therefore it is possible by means of the climatic control actually to carry out a deactivation process in the activation chamber for maintaining and saving the cover serving as piece of equipment, also in the case that it is unused over a longer period of time.

It is also described here to be advantageous that the activation chamber has a control element interacting with the moisture activating element and with the cover, and that the control element controls the moistening device. Besides this control of moistening, of course, even other processes are possible by the use of the moisture activation element. The data interface nay be increased accordingly, and, besides the control element, other information can be evaluated. Depending on this information then other processes, for example, drying processes, maintenance processes or the like can be started. Conveniently, a status indicating device of the climate prevailing in the interior or the cover in the interior is provided. By means of this it is possible to see from the outside whether a certain cover is already prepared for operation or not. This information may be received by a measuring of the moisture at the cover itself or a display of the status of the climate in the interior. The invention can be applied in this case very variably.

By the use of this control, for example, via a store programming control (SPS) the connection to a tele-maintenance unit in the company can be guaranteed. Thus centrally one or more activation chambers can be controlled and maintained.

Thus in a preferred modification of the invention it is provided that the control element has a communication unit, in particular with a transmitting and reception antenna for the exchange of data with the information circuit of the cover. At this point it is referred to the respective design of the information circuit in the cover. Via these two antennas a corresponding communication channel is operated, and allows a wireless data exchange. The same can, of course, also be carried out, as described, by means of a wire connection, then for example, a plug contact has to be connected accordingly.

Via this communication channel then, for example, first of all, the authorization of the suspended cover is inquired. For that purpose, first of all, for example, the definite identification number of the data memory of the information circuit is read out and transferred in the control element. There this information is compared with a data bank existing there where all licensed and authorized identification numbers are stored. If incidentally a not-authorized cover is hung in, either corresponding information is transmitted, or a loading or activating process is not started.

Here the access to the data memory with the stored identification number is not restricted only to a corresponding check of the authorization, because of this information also a monitoring of the respective cover is possible without any problems. Thus, for example, by means of that the number of loading cycles can be monitored. Furthermore it is possible to call and file via the communication channel described before sensor values stored in the data memory, and then also to process them later. Thus, for example, because of the operation procedure it is possible to draw conclusions about a possible damage of the cover. Of course, it is also possible via the communication channel to call physiologic data stored in the information circuit, and to assign to the user file known via the file of the covers.

Furthermore the invention provides that at least one loading sensor is provided which monitors the degree of activation of the cover or the amount of liquid passed in the cover, and the load sensor interacts with the control element. The activation or loading process is triggered by recognizing a cover hung in the activation chamber, for example by means of the activation element (mechanical or electro-magnetic). In order not to risk over-loading of the cover a load sensor is provided which finally controls in the same way the supply of liquid, and if necessary, even stops it. For that purpose the over-load sensor interacts with the control element.

Conveniently the load sensor is designed as mass, weight or moisture sensor. It is designed, for example, as weight sensor at the holding device carrying the covers.

Furthermore it is provided that the activation chamber has one or even two or more interior spaces which can be separated from each other. In constructive respect this can be realized by two identical, symmetric cabinet halves which have a common side part. Thus it is, for example, possible, that one side is just in the process of activating (moistening by water), the other side already stores materials dry on the outer shell and ready for use. This is also carried out fully automatically in a specific frequency so that the user can already recognize from the outside of the cabinet which garments or other materials are ready for use. The result is thus a supply ready 24 hours around the clock.

As both sides of the cabinet are set in such a way that always one side has prepared “outer shell dry”, liquid-drenched materials, the entire cooling system is always and permanently ready for use.

Cleverly each interior space of the activation chamber can have its own climatic control, or the climatic controls of the interior spaces are independent from each other. However, also a common control can be used. Here it is, of course, also possible to assign to the activation cabinet additionally also a pure drying function, for example, for wet gear which is not designed like a cover. Thus the activation cabinet also fulfils another useful task which is just in the professional field (life saving or fire brigade) an advantage as all pieces of equipment per person can be stored and prepared clearly laid out at one place.

Conveniently a status indicating device of the climate prevailing in the interior or the cover in the interior is provided. The cover, for example, carries sensors measuring the degree of moisture in the cover. This information received here is provided, for example, for the user as status indicating device. With the same sensors, however, it is now possible to monitor the respective loading condition in the cover which is just again being filled in the activation cabinet with liquid or moisture. This can be done, of course, also by means of the load sensor or a weight sensor or a weight difference sensor. It is also possible to set a certain protective gas atmosphere in the interior of the activation chamber which is then indicated also via a suitable status indicating device, and thus, for example, helps preventing an unintended opening of the activation chamber. Of course, also the door of the activation chamber can be locked a limited time during corresponding rinsing or cleaning processes.

The climatic control provided according to the invention interacts here, of course, with suitable sensors through which the prevailing climate (air moisture, if necessary gas composition, and also temperature) is measured and determined. In particular, via the quality of the used air it can be assessed here whether in the meantime the drying process has been finished accordingly.

Here it is provided according to the invention that the control element which actually interacts with the activation element is designed for the climatic control each time as separate controls or is realized as part of a bit larger or more complex cabinet controls. The integral as well as the modular construction are part of the invention.

In a preferred embodiment of the invention it is suggested that the cabinet control, the control element and/or the climatic control are designed as store programming control. Such an embodiment of the control makes it possible to adapt the control comparatively easy to altered conditions. It is provided here cleverly to design the complete cabinet control, which thus comprises the control element as well as the climatic control, as store programming control, or, if necessary, only the control element or only the climatic control. The invention is not restricted in this respect.

It is an essential advantage that the cabinet control, the control element and/or the climatic control have a tele-maintenance unit. By means of such a tele-maintenance unit, which is eventually an interface from the outside in the cabinet control or the control element or the climatic control, it is possible to change corresponding adjustments or programme processes in the control. Exactly the realization of the cabinet control as store programming control supports this advantage. Furthermore, however, the tele-maintenance unit makes it also possible that in the control new, permissible identification numbers of jackets or covers which have to be loaded or maintained are supplemented. If the user buys additional, new covers—for example a fire brigade enlarges its supply of suitable protective jackets—these new jackets may be reintroduced by transferring the necessary information via the tele-maintenance unit in the cabinet control, the control element or the climatic control. The system according to the invention then also is available for these covers. The same goes, of course, also for introducing of suitable parameters or the additional set-up of inquiry routines, for example with regard to wear and so on. An essential advantage of the use of a store programming control is the fact that the comfort for operating is increased accordingly. It is, for example, possible without any problems to vary the respective drying or moistening cycles. Also the safety or emergency switch can be imaged by the store programming control, that means by a suitable key assignment the emergency stop is activated. Also a tele-maintenance can be operated by means of the store programming control without any problems.

Conveniently an air or gas recycling is provided, for example, in order to dry, clean or filter the air or gas, if necessary even to cool or heat.

Furthermore the activation chamber consists, for example, of a top and a bottom cabinet, the top cabinet being produced, for example, from steel sheet of 1.5 mm thickness or other materials.

Conveniently it is provided that the activation chamber has at least one moisture collecting basin. This moisture collecting basin serves for collecting moisture which may escape, for example, from defect covers. For each chamber, if necessary, also several basins can be used, for example per cabinet or shelf one collecting basin each. The moisture collecting basin is here connected with a drain for disposing off the escaped liquid, or it is designed in such a way that the liquid escaped in this way can be used again.

Cleverly a level sensor for the level of moisture in the moisture collecting basin is provided, for example, for stopping in the frame of an emergency circuit the supply of more liquid in the activation chamber.

According to the invention also the use of a drying device in the activation chamber is provided. Here the invention comprises not only the moistening device, as described, or only the drying device, but it can very well comprise both components, so that, for example, in a suitable way a combined moistening or drying is reached in such a way that the result is a filled cover which is not uncomfortably wet at its surface but dry.

Here according to the invention it is suggested that the drying device is designed as hot air dryer, infrared (IR) radiation dryer or as immersion heater and so on. Such drying devices can be realized economically and are sufficient for the intended purpose.

On the one hand it is provided here that the course of the (warm) air in the activation chamber is from the bottom to the top or from the top to the bottom. Here the warm air is blown with a hot air or warm air drying device from the bottom in the activation chamber, and then passes the covers upstairs and is sucked off at the top. The activation chamber here can also provide an air drying device, or the air is released to the air of the environment similar to a laundry dryer. Of course, the course of the air can also be directed in other directions or backwards.

In an embodiment of the invention additional heat elements are provided which then have, for example, other drying tasks. These may be additional, in particular, complete drying of articles of equipment or objects like shoes, gloves and so on.

For a use of the covers as effective and also hygienic as possible it is provided that the covers are maintained periodically, for example a suitable cleaning process is part of that. For that purpose it is, for example, provided, that the moistening device flushes for cleaning or maintenance purposes a cleaning or disinfectant liquid in the cover. A suitable disinfectant process can also be reached, for example, by a protective gas atmosphere. For removing the cleaning or disinfectant liquid suitable rinsing steps, if necessary under the use of a suitable warming application for drying the liquid from the super absorber are provided.

The activation chamber is advantageously designed as a cabinet, however, not restricted to that. The activation chamber can be realized, for example, also as chest-of-drawers or trunk-like device.

In a preferred modification of the process according to the invention it is suggested that, before the activation, a cleaning step and/or a drying step of the cover, in particular of the fleece in the cover, is provided. By such a procedure, which may be called a deactivation step, for example, first of all a complete drying of the cover is achieved, which is really convenient, for example, for cleaning purposes or hygienic reasons. Separated from it or connected with it there may be a cleaning step which can be carried out, for example, with a suitable disinfectant or cleaning liquid. It is again convenient here that, if necessary, after a cleaning step, a drying is carried out, and then, with one or more rinsing steps with water, each time followed by drying steps, a cleaning or disinfection is carried out. It is convenient here to carry out one or more cycles of cleaning and drying steps after that in order to remove the liquid stored in the super absorber reliably. For an effective drying, for example, through the ventilation channels or the channels serving for liquid supply warm air is blown.

Furthermore it is suggested according to the invention that a clockwise moistening or watering or a moistening or watering in batches of the cover is carried out. By means of such a procedure the loading of the cover with liquid is made accordingly easier as the liquid has accordingly time to spread in the fleece, and, in particular in the zone of the supply or in the permeability area, there will be no backpressure of liquid. In addition to that the expenses for the liquid are less. In the watering breaks a corresponding measurement of the weight cam also be carried out.

The invention is not limited here to a special way how the moisture is passed in the cover. It is, for example, also possible to spray the cover clocked, and, in the breaks, to give the liquid the possibility to be absorbed by the material. However, also a continuous moistening is possible. Thus the invention also provides a continuous, but also a clocked moistening or a moistening in batches or a watering of the cover. When the moistening is clocked, for example, during a first period of time a watering or moistening of the cover is carried out which is then, within a second period of time, switched off in order to reach that the liquid in the cover is distributed accordingly and absorbed in the super absorber. A moistening in batches differs from a continuous moistening by the fact that with a moistening in batches in a short time a larger amount of liquid is passed in the cover, whereas with a continuous moistening a smaller liquid stream flows in the cover during a longer period of time. The cleverest embodiment of this moistening step, of course, depends on the design of the cover, according to its permeability area, but also on the absorption capacity and the absorption capacity of the fleece material absorbing the liquid. The method according to the invention can be adjusted to that in a suitable way.

The same is, for example, also provided when the cover is suspended on a holding device.

Conveniently it is provided that starting and activating is done automatically as soon as the cover gets in an activation chamber, and the activation chamber has been closed, or a corresponding switch has been operated. Thus, for example by means of hanging the cover designed as vest or jacket in the cabinet, activating is triggered, for example by the interaction of the activating element arranged at the cover with the control element of the activation chamber.

Furthermore according to the invention it is suggested that, after putting the cover in an activation chamber, an identification or authorization of the cover is carried out. This should exclude, for example, that non-authorized covers, hung in the activation chamber, are activated possibly not in a suitable way.

The invention makes a complex management of the cover possible. This is done by evaluating the data which are produced by the information circuit provided at the cover. By means of that it is, for example, possible, if the cover has been used in contaminated areas, first of all, to select another activating programme than the usual one. Therefore the invention provides that several different activation programmes can be carried out, and the selection of the activation programme is done depending on the identification of the cover. By identifying the cover as well as evaluating the other data of the cover programme controlled the suitable activation programme is chosen and used.

In this connection it is, in particular, pointed out that all characteristics and properties described with reference to the cover or the activation chamber, but also methods according also to the formulation of the method according to the invention are seen as being able to be transferred and applicable and also disclosed in the sense of the invention. The same goes also vice versa. This means constructive, that means subject characteristics mentioned only with reference to the method may lead also in the frame of the claims to claiming the activation system, the activation chamber or the cover, and also are part of the invention.

Advantages of the Invention:

- First cooling system which combines the advantages of cooling by super absorber materials with practicable and always ready-for-use activation, drying and storing system.
- Heat protection by cooling through the use of specific and practicable super absorber materials which do not drain off and can be processed easily.
- Very light and flexible super absorber material, and thus simple and easy transport or storing of the clothing and equipment or blankets, tarpaulins and covers.
- Natural and long-lasting cooling effect by evaporation of the water bound in the material up to 5 to 30 times or more of its weight without yielding it by mechanical pressure. Thus a much longer cooling effect is reached of up to 8 to 60 hours depending on the temperature of the environment.
- Possibility for producing of fireproof and hardly inflammable materials.

Of course, different fleece materials with a different thickness as well as capability of binding water can be produced and used depending on the requirements of the respective persons in charge during heat fighting measurements. By a larger thickness of the material or larger amount of the super absorber coating of the fleece the degree of the capability of binding water changes upwards. Of course, thus the weight of the dry fleece per area increases, however, this occurs only at a small scale and thus has hardly any effect on the handling.

When the amount of coating is high, however, the mechanical stability of the material in moist conditions increases so that by means of that actually a mechanical carrying capacity exists what can actually be an advantage in the frame of fire fighting. A strongly coated material in moist condition has a stability similar to flexible synthetic material (“rubber”), and resists strong mechanical stress (for example hail, falling or whirling objects, for example in explosions etc.) By the “rubber-like” consistency blows and mechanical influences from the outside are absorbed.

In the following several examples of the cover according the invention are described with more detail:

The cover may be, for example, realized as a garment in very different modifications. Thus here, for example, vests, headbands, trousers, jackets and so on are possible.

Cooling pads as covers inserted in clothing or equipment which themselves contain the described material, for example in baseball caps, hats, helmets, caps to put on underneath helmets, etc. attached with suitable connection means as for example snap or VELCRO hook and loop fasteners or the like.

Heat protection on rollers for large-scale operations and individual size adjustment for fire brigades and authorities.

Finished coverings and covers in different shapes and sizes for the fast instantaneous operation.

Medical products, for example, surgery blankets or cooling pads for cooling of blunt injuries and bruises.

Loading or activating in the sense of the description of this application is understood here that the cover is filled with moisture or water or other liquids, that means it is loaded. As by the continuous effect of water evaporation during the operation according to the purpose water evaporates from the cover according to the invention for cooling purposes out of the super absorber, by activating or loading exactly this water or liquid is brought back in the cover again, whereby the activation may also comprise drying of the surface as described, but it is not compulsory.

For improving maintenance it is, in particular, provided, for example, to rinse in liquids with disinfectants in the covers and to remove them again by rinsing processes. By the application of such rinsing steps it is also possible to keep the covers as hygienic as possible. The application of these rinsing steps is determined, for example, by the climate automatic or climatic control.

The term cover has to be understood here not only in that a person or an article is enclosed entirely by the cover, but the term cover is, according to the invention, for example, also to be understood and defined as covering, that means not entirely enclosing. The range of use of the invention is not restricted to the described case. Besides the described use, in particular in work protection or fire fighting, it is, of course, also provided to use the invention in the field of sports or leisure time. Here also it is sometimes convenient to have a suitable cooling effect. It is also possible to use the invention, for example, in countries with a hot climate where the use of air conditioning is not possible. By means of the invention still a certain cooling effect is reached, and thus also an increase in performance of the user. Therefore the invention is not restricted only to the field of use of protection in work, heat or fire, it rather extends also to the fields of use in leisure time or commonly for increasing the well being, just with high temperatures.

V. BRIEF DESCRIPTION OF THE VIEWS OF THE DRAWING

Figure 2:
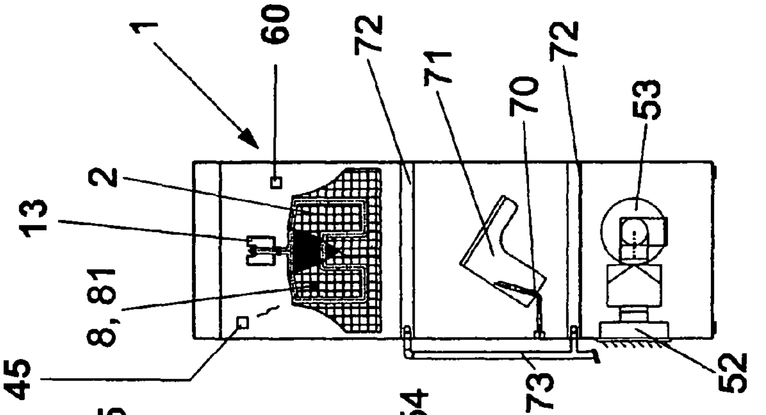
Figure 1:
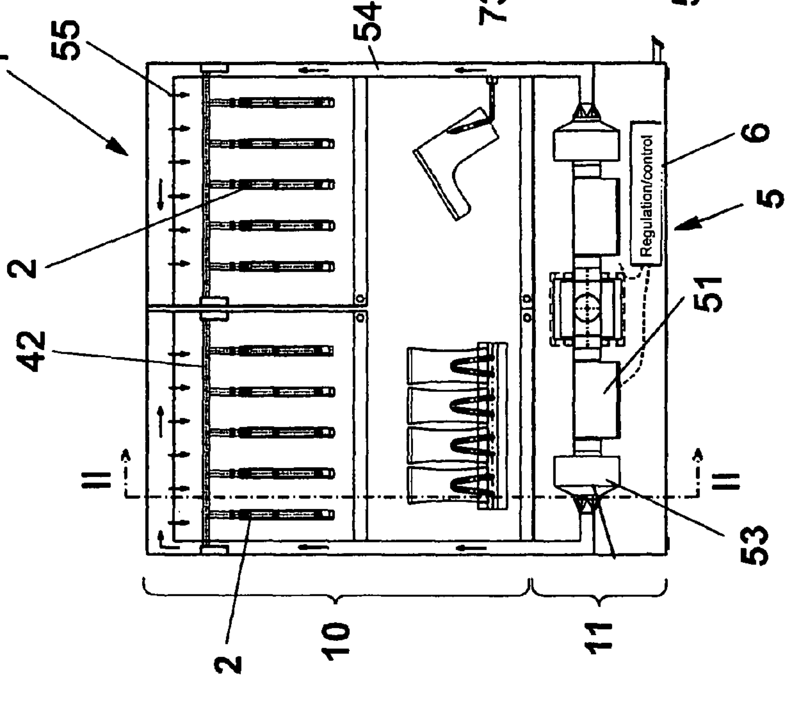
Figure 4:
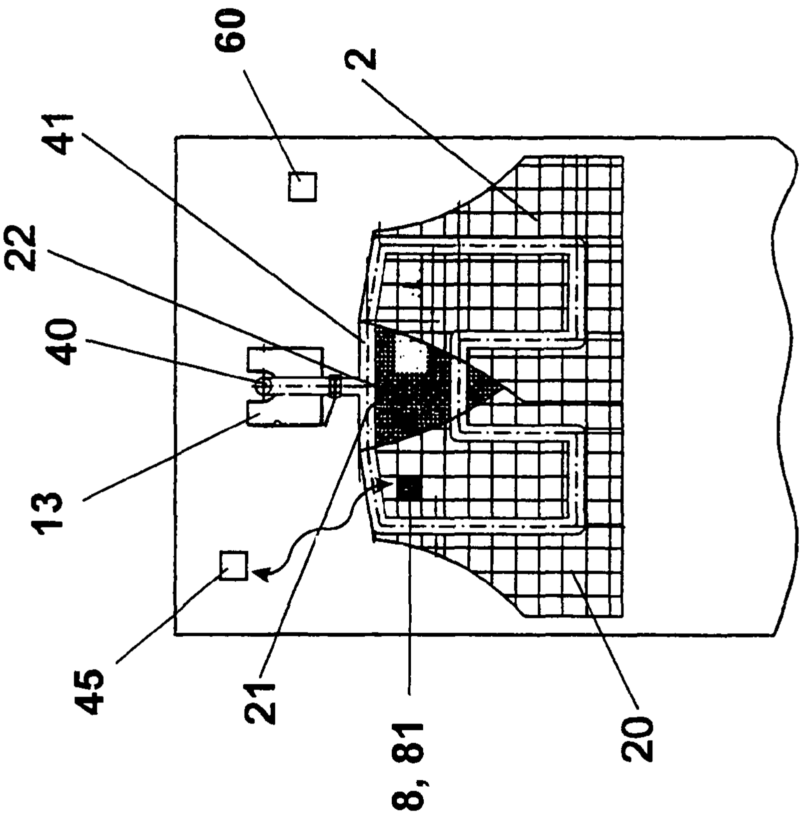
Figure 3:
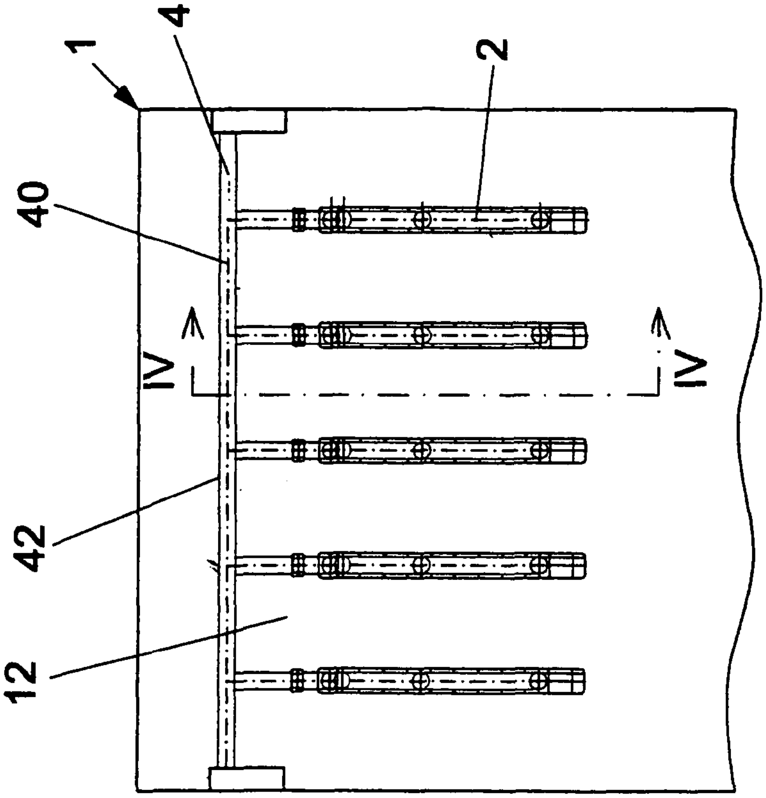

In the drawing the invention is shown schematically. In the drawings:

FIGS. 1, 3 each a view of a modification of the activation chamber according to the invention and FIGS. 2, 4 each a horizontal section of FIG. 1 or FIG. 3 according to the lines II-II, IV-IV in FIGS. 1, 3.

Figure 5:
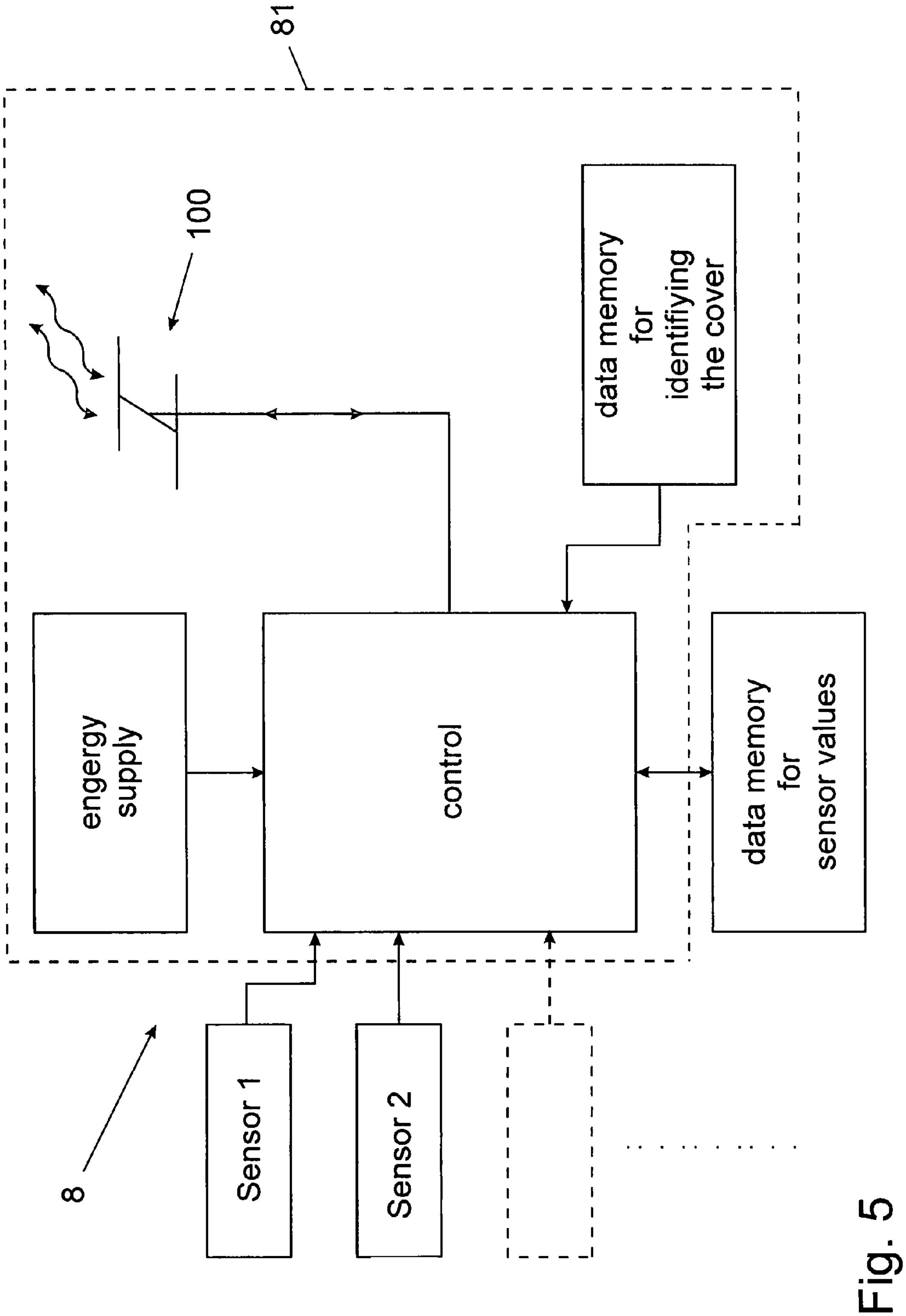

FIG. 5 In a block diagram the basic design of the information circuit of the cover according to the invention.

Figure 6:
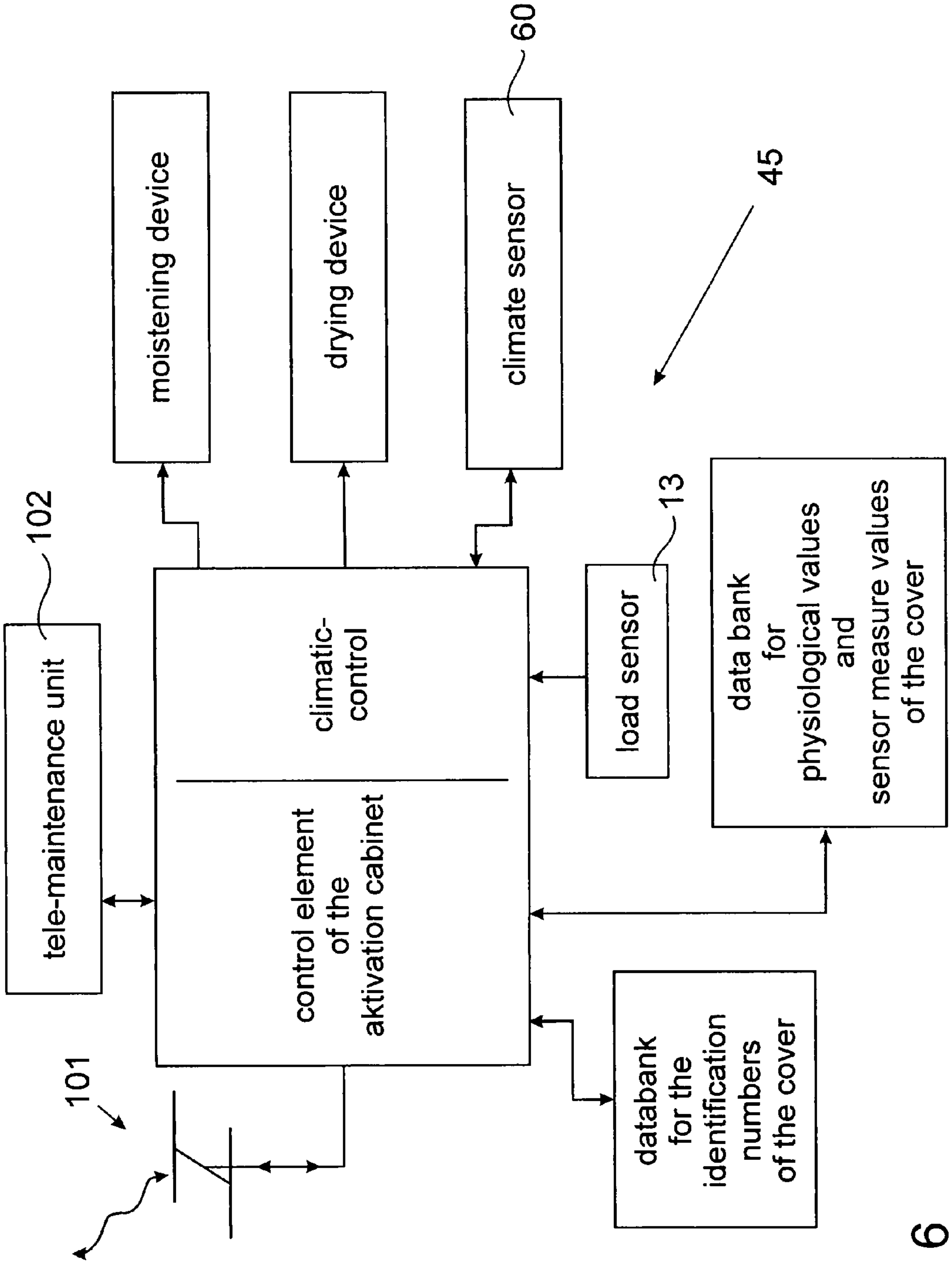

FIG. 6 In a block diagram the chamber control of the activation chamber according to the invention.

Figure 7:
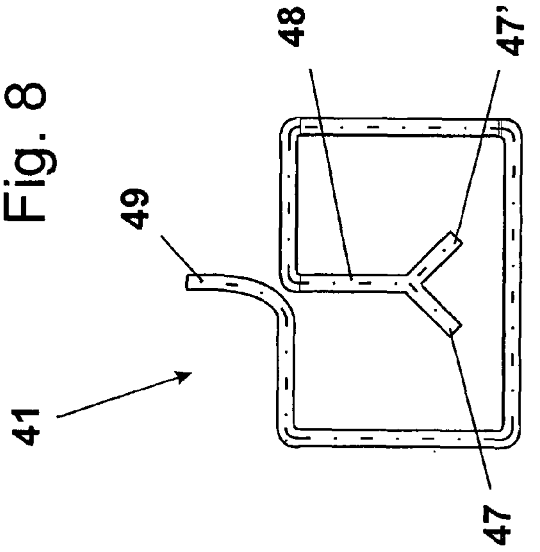

FIGS. 7, 8 each an alternative embodiment of the holding device according to the invention.

VI. DESCRIPTION OF THE PREFERRED EMBODIMENTS

FIG. 1 shows schematically the activation chamber 1 according to the invention. The activation chamber 1 comprises a top cabinet 10 and a bottom cabinet 11. The top cabinet 10 is, for example, equipped with a basin made from stainless steel as moisture collecting basin, and has a rail holding device 42 where the holding devices 41 carrying the covers 2 are provided.

A shelve with heating elements 70 for other pieces of equipment, like for example shoes 71 is provided below.

Below the area where the covers 2 are suspended or the shoes 71 are arranged, each time a moisture collecting basin 72 is provided. The moisture getting there is disposed off by the drain 73.

In the examples shown here the activation chambers 1 are opened, suitable flap doors are provided which are also equipped with windows, if necessary. The arrangement at the activation chamber 1 is done here in such a way that it can be sealed tightly in order to reach in particular a climate cutting-off for the interior space 12 of the activation chamber 1.

In the area of the bottom cabinet 11 the technical devices are stored, for example, in a technical cabinet. Here also doors, if necessary even lock-up doors, are provided. The complete activation chamber 1 is supported, for example, on feet non-skidding or also alternatively on rollers.

The technical devices for the activation chamber comprises essentially three elements, namely the climatic control 6, a drying device 5 and a moistening device 4.

The drying device 5 here consists of a fan 53 which takes in air from the outside and cleans it through one or several suction filters. Through a heating or a heating cartridge 51 the air thus recycled is conveyed via tubes 54 to different places of the interior space 12. Small arrows 55 indicate inlet openings 55 through which the hot air gets in the interior space 12. Corresponding ventilation openings are not shown through which the conveyed-in air, if necessary, accordingly moistened and also cooled, can leave again.

For the control and regulation of the drying device 5 the climatic control 6 is provided which is connected with several sensors not shown here in particular, and according to the measure values and the given set values acts on the drying device 5 as well as on the moistening device 4.

The moistening device 4 is shown and described in particular in FIGS. 3 and 4. The moistening device 4 comprises in particular holding devices 41 which are, similar to the rail holding device 42, hollow. The hollow rail holding device 42 as well as the hollow holding device 41 pass the water or generally the liquid required for loading the covers 2. The holding device 41 is, in particular, designed hanger-like in order to be able to suspend on it a cover designed for example as jacket 20.

The suspended jacket 20 thus forms an internal, pocket-like recess 21, the interior lining of the jacket 20 has a permeability area 22 through which the liquid can penetrate easily and simply in the cover 2. Thus the super absorber of the cover 2 is loaded with water.

The holding device 41 has a number of small openings so that the water conveyed in the recess 21 can pass to the permeability area 22 of the cover 2. The water is here transported via the tube system of the moistening device 4 through the tube 40 of the rail holding device 42 in the holding device 41, and then passes through openings in the cover 2.

An easy assembly is provided by a screw connection between the holding device 41 and the rail holding device 42.

A load sensor 13 is shown schematically in FIG. 4 or 2 in the upper region of the holding device 41.

It is hinted that the jacket 20 carries an information circuit 8 or a moistening activation switch 81. In the situation shown here the jacket 2 is suspended in the activation chamber 1, and between the information circuit 8 and the control element 45 a radio connection is set up (indicated by the sinus-shaped wave).

In the block diagram of FIG. 5 the information circuit of the cover is shown schematically.

The core of the information circuit is the control. It is, for example, designed as micro controller or micro processor, and controls the flow of data between the single elements.

By means of an energy supply the control and the connected elements are supplied with energy. The energy supply is, for example, designed as battery or as chargeable accumulator. However, it is also possible, that a capacitor serves as energy supply which is designed via the transmitted electromagnetic energy received by the transmitting/reception antenna 100.

By means of the transmitting/reception antenna 100 the data exchange with the transmitting/reception antenna 101 of the control element of the activation chamber 1 is carried out.

The connection between the control and the transmitting/reception antenna 100 is bi-directional, that means information may be received here for the control as well as sent.

For example, by a data memory for the identification number of the cover the respective defined identification number is read out by the control, and if required, that means on demand of the control element, passed on through the transmitting/reception unit 100.

This is carried out, for example, when the cover is hung in the activation chamber with the information circuit designed in FIG. 5.

During the use of the cover one or more of the sensors will transmit corresponding sensor values to the control which are filed by it in one of the data memories for sensor values. Also the connection path between this data memory and the control is bi-directional as the here memorized values are transmitted, for example on demand of the control element also via the transmitting/reception unit. The activation element, as it is described for example, would consist, for example according to FIG. 5, of the data memory for the identification number of the cover, the control as well as the transmitting antenna 100. Of course, also the energy supply is part of it. This may be, as described, active or passive, that means in the passive case the arrangement becomes active only when corresponding electro-magnetic energy is received. This is known as so-called RFID technology.

In FIG. 6 the cabinet control of the activation chamber is shown schematically. The cabinet control comprises here as central element a control element as well as a climatic control. These can, as described, be designed as modules, or be integrated.

Via the reception/transmitting antenna 101 the data received by the information circuit (see FIG. 5) are received and evaluated by the control element. For that purpose, for example, the control element transmits periodically a suitable calling signal via the transmitting antenna 101, and then waits for a corresponding answer of the information circuit. If then a corresponding answer signal is received the control element inquires the identification number of the respective cover, and compares the then received information with the entries in a data bank or a data memory for the identification numbers of the covers.

The data line from the antenna 101 to the control element as well as between the data bank for the identification numbers and the control element are designed bi-directional.

After a corresponding authentication or authorization test has been concluded positively, that means that the corresponding identification number has also been found in this data bank, the control element activates the moistening device which is designed, for example, as shown in FIG. 4. It is possible here that the moistening device is called either indirectly by the climatic control or directly by the control element of the activation cabinet.

It is possible to run an individual activation programme for the cover. For that purpose the historical values are checked from a corresponding data memory, and, after that, evaluated according to respectively adjustable criteria which activation programme or, if necessary, also care or maintenance programme should be provided for this cover.

Also physiologic values transferred via the communication channel formed by the transmitting/reception antennas 100, 101 which are supplied in the corresponding data memory of the information circuit can now be entered in the respective data bank and be supplied for evaluation purposes.

In the simplest modification according to the invention, however, it is provided that by the activation element of the information circuit or the cover or a time allowance control the moistening process is started, and thus activates the control element of the moistening device. For that purpose, for example, a suitable valve is opened. This can be controlled, for example, by a load sensor 13 which for example first detects whether really a suitable cover is suspended on the chosen holding device, and on confirmation, actually opens the valve. Wasting of liquid and so on is thus avoided.

Parallel or after the moistening then drying of the surface of the layer is done. If, in particular, the cover is worn in work protection of persons, by a corresponding drying of at least the layer in contact with the body or the clothing a comfortable wearing is reached. As described the drying process can follow the moistening or be parallel, the climatic control monitors the drying and for that purpose the climatic control is in connection with suitable climate sensors and monitors, for example, the quality or the physical properties of the used air. However, the use of the climatic control is not restricted to that. The climatic control interacts with climate sensors which, for example, inform about the gas composition. Basically it is possible also to establish more complex monitoring cycles, and, for example, by an inert gas cleaning and so on, to carry out suitable cleaning, caring or maintenance steps for the cover. Also rinsing processes and so on may be carried out by an accordingly more complex design of the cabinet control.

The load sensor does not only release the valve for moistening by the moistening device, but it also closes the valve again when a suitable amount of liquid has been passed in the cover. The loading degree may be adjusted individually. The load sensor is designed, for example, as electronically active weight sensor, a sensor control connected with it defines the starting and final weight, and determines from this difference the degree of loading which is monitored for filling.

Cleverly the cabinet control or the control element or the climatic control is connected with a tele-maintenance unit 102 or is equipped with one. Via this tele-maintenance unit eventually an interface exists for maintaining the control, for example by feeding a new programme in the store programming control, or for downloading or actualizing the data bank for the identification numbers of the covers. Thus it is, for example, possible to feed the system with new identification numbers.

For a distribution of the liquid in the cover as effective as possible, according to FIG. 7 a modification of the holding device 41 according to the invention is suggested.

The holding device shown here is essentially designed rectangular, a perforated tube being designed frame-like uncoiled. One end of the frame is connected with the tube system 40 not shown here in detail. This end of the holding device is indicated with 49. In the following, the tube is designed angled essentially rectangular, the end 48 opposite the tube system being designed angled to the interior of the frame, and fanned out in two or more distribution branches 47, 47'. By such a design an effective and also large-surface introducing of the liquid as fast as possible in the permeability area of the cover is reached.

In contrast to the modification according to FIG. 7, in FIG. 8 an alternative holding device 41*a* is shown. The basic arrangement of the holding device 41*a* is already very similar to the one in FIG. 7. Here it is also provided, for example, that the tube is designed perforated. However, the basic shape of this holding device 41*a* is oval-shaped or elliptic with larger radius, whereby in the embodiment shown here the lateral ends are formed by half-circles. In the end zone of the holding device there is no branching provided here, but the tube simply runs out. If necessary, also the end of the tube is equipped with a perforation, according to the diameter of the rest of the tube.

By means of the larger radius used here also hanging on and off the covers or jackets or specially designed garments is made easier according, to the invention.

The invention of a cooling system for heat protection and cooling at higher temperatures by use and combination of a climate drying cabinet with materials containing a synthetic fleece coated with super absorber is a new process. Here the immediate and permanent readiness for use of the cooling materials is achieved which overcomes all disadvantages known so far with regard to effort, time and practicability, and adds other advantages not known so far.

The cooling materials are moistened in the climate drying cabinet, absorb water during that and drain it off during the use at high temperatures by evaporation so that by the occurring latent heat a desired cooling effect occurs for the object or person to be protected.

The objects or persons to be protected against high temperatures remain cool, are not exposed too much to high temperatures, but they get a cool climate. By means of the shock absorbing property of the materials in moist condition the objects and persons to be protected can additionally be protected against mechanical interference, for example falling objects from the outside.

The specific absorber material is designed in such a way that it justifies a permanent and long use, it can be processed easily and can also be used in mass production.

The cooling system achieves by the use of the climate drying cabinet a comfort which guarantees the permanent, safe and immediate use of the materials. Just in the case of a sudden and immediate use, like the one of a fire brigade operation, the super absorber cooling system or the activation system becomes now practicable, and a cooling of the fire fighters exposed to the high temperatures is possible. This was impossible until now as the effort with regard to the super absorber materials was much too large and not compatible with an immediate and possibly long saving operation.

The fully automatic and permanently ready-to-use system will be an enormous step forward with regard to health and safety during heat and high temperatures in a lot of fields. The term activation system can be seen as identical with the term cooling system in this application. The system comprises not only the idea of an effective activation but also the aspect of an effective cooling. If necessary this system can refer to one or more of the characteristics of the cover mentioned before, or the activation chamber and also to the method.

The claims filed with the application now and to be filed later on are attempted formulations without prejudice of obtaining a broader protection.

If here, on closer examination, in particular also of the relevant prior art it turns out that one or the other feature may be convenient for the object of the invention, however, not decisively important, of course, already now a formulation is striven for which does not contain anymore such a feature, in particular in the main claim.

Further, it has to be taken into consideration that the embodiments and modifications of the invention described in different examples and shown in the figures, can be combined with each other at will. Individual or several characteristics can be exchanged at will. These combinations of characteristics are disclosed as well.

The references in the sub-claims refer to the further design of the matter of the main claim by the characteristics of the respective sub-claim. These are, however, not to be understood as a waiver of independent protection of the matter for the characteristics of the referred sub-claims.

Characteristics only disclosed in the description so far may now, in the course of proceedings, be claimed as being of inventive relevance, for example to distinguish from the state of the art.

Characteristics only disclosed in the description or even single characteristics from claims which comprise a variety of characteristics may be used at any time to distinguish from the state of the art in the first claim, and this even if such characteristics have been mentioned in connection with other characteristics, or achieve particularly convenient results in connection with other characteristics.

The invention claimed is:

1. A cooling system comprising a cover having a top layer, a bottom layer and a layer of fleece, said layer of fleece being arranged to extend over an entire area between the top and the bottom layer, and said layer of fleece being fixedly coated with a super absorber for absorbing moisture or liquid, both of the top layer and the bottom layer having at least an area of permeability, permeable to liquid in order to uniformly moisten the layer of fleece with a controlled amount of liquid, and a liquid directing device to control a predetermined amount of liquid introduced uniformly into the cover, a chamber including a closed interior space for holding one or more covers, the chamber having the liquid directing device for controlled moistening of the cover through the area of permeability, and a drying device for a superficial drying of only an exterior surface of the cover, the cover being located in the chamber with a controlled amount of moisture so that the cover has a cooling potential when the cover is removed from the chamber because of evaporation heat necessary for evaporating the loaded moisture.

2. A method for introducing water into a cover having a top layer, a bottom layer and a layer of fleece, said layer of fleece being arranged to extend over an entire area between the top and bottom layer, and said layer of fleece being fixedly coated with a super absorber for absorbing moisture or liquid, both of the top layer and the bottom layer having at least an area of permeability, permeable to liquid in order to uniformly moisten the layer of fleece with a controlled amount of liquid, and a liquid directing device to control a predetermined amount of liquid introduced uniformly into the cover, said method comprising the steps of controlling a defined amount of liquid flow uniformly into the cover by the liquid directing device, and superficially drying only the top layer of the cover so as to produce a dry exterior surface of the cover and a liquid saturated layer of fleece, for using and thereby cooling by evaporative removal of heat by liquid from the super absorber.

3. The method according to claim 2, wherein before controlling, a cleaning or a drying step of one of the layers, is provided.

4. The method according to claim 2, further comprising a continuous, timed moistening, or moistening of the cover in batches where an automatic wetting begins as soon as the cover is in a closed interior space.

5. The method according to claim 2, wherein after the cover has been put in a closed interior space, an identifying of the cover is carried out and several different moistening programs are selected, and selection of the moistening program is done depending on an identification of the cover.

6. The method according to claim 2, wherein after putting the cover in a closed interior space an identifying of the cover is carried out, and after identifying the cover physiological data and sensor measured values are transmitted by an information circuit of the cover in a data memory of a cabinet control.

* * * * *